(12) United States Patent
Wu et al.

(10) Patent No.: US 9,439,585 B2
(45) Date of Patent: Sep. 13, 2016

(54) SEMICONDUCTOR BASED ANALYTE SENSORS AND METHODS

(75) Inventors: Mu Wu, Hopewell Junction, NY (US); Jiangfeng Fei, Sleepy Hollow, NY (US); Serban Peteu, East Lansing, MI (US); Hoi-Cheong Steve Sun, Mount Kisco, NY (US); Raeann Gifford, Cortlandt Manor, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 246 days.

(21) Appl. No.: 12/864,277

(22) PCT Filed: Feb. 3, 2009

(86) PCT No.: PCT/US2009/032991
§ 371 (c)(1),
(2), (4) Date: Jul. 23, 2010

(87) PCT Pub. No.: WO2009/100082
PCT Pub. Date: Aug. 13, 2009

(65) Prior Publication Data
US 2010/0298679 A1  Nov. 25, 2010

Related U.S. Application Data

(60) Provisional application No. 61/026,081, filed on Feb. 4, 2008.

(51) Int. Cl.
*A61B 5/05* (2006.01)
*A61B 5/145* (2006.01)
*A61B 5/1486* (2006.01)

(52) U.S. Cl.
CPC ....... *A61B 5/14532* (2013.01); *A61B 5/14865* (2013.01)

(58) Field of Classification Search
CPC ................... A61B 5/14532; A61B 5/14542
USPC ................... 600/354, 347, 345, 365, 348
See application file for complete search history.

(56) References Cited

U.S. PATENT DOCUMENTS

| | | |
|---|---|---|
| 4,326,927 A | 4/1982 | Stetter et al. |
| 4,596,741 A | 6/1986 | Endou et al. |

(Continued)

FOREIGN PATENT DOCUMENTS

| | | |
|---|---|---|
| WO | WO 2006/057722 | 6/2006 |
| WO | WO 2009/100082 | 8/2009 |

(Continued)

OTHER PUBLICATIONS

Schackleford et al., CRC Materials Science and Engineering Handbook, 3rd ed., 2000, Table 154.*

(Continued)

*Primary Examiner* — Michael Kahelin
*Assistant Examiner* — Tho Tran
(74) *Attorney, Agent, or Firm* — Dugan & Dugan, PC (57) ABSTRACT

An analyte sensor is provided that comprises a substrate which includes a semiconductor material. Embodiments may include a core of a conductive material, and a cladding of a semiconductor material, in which the cladding may form at least a portion of a conducting path for a working electrode of the analyte sensor. Method of manufacturing and using the analyte sensor are described, as are numerous other aspects.

15 Claims, 4 Drawing Sheets

(56) References Cited

U.S. PATENT DOCUMENTS

| | | |
|---|---|---|
| 5,223,124 A | 6/1993 | Ege |
| 5,338,415 A | 8/1994 | Sailor et al. |
| 5,352,348 A | 10/1994 | Young |
| 5,431,800 A | 7/1995 | Kirchhoff et al. |
| 5,476,776 A | 12/1995 | Wilkins |
| 5,593,852 A | 1/1997 | Heller |
| 5,611,900 A | 3/1997 | Worden et al. |
| 5,627,922 A | 5/1997 | Kopelman et al. |
| 5,634,913 A | 6/1997 | Stinger |
| 5,700,695 A | 12/1997 | Yassinzadeh et al. |
| 5,777,372 A | 7/1998 | Kobashi |
| 5,866,353 A | 2/1999 | Berneth |
| 6,132,893 A | 10/2000 | Schoning |
| 6,176,988 B1 | 1/2001 | Kessler |
| 6,218,661 B1 | 4/2001 | Schroeder et al. |
| 6,521,109 B1 | 2/2003 | Bartic et al. |
| 6,521,110 B1 | 2/2003 | Hodges |
| 6,695,958 B1 | 2/2004 | Adam |
| 6,726,818 B2 | 4/2004 | Cui |
| 6,743,635 B2 | 6/2004 | Neel et al. |
| 7,951,632 B1 | 5/2011 | Quick et al. |
| 8,202,697 B2 | 6/2012 | Holmes |
| 2002/0137998 A1 | 9/2002 | Smart et al. |
| 2002/0168290 A1 | 11/2002 | Yuzhakov et al. |
| 2002/0177763 A1 | 11/2002 | Burns et al. |
| 2003/0088166 A1 | 5/2003 | Say et al. |
| 2003/0135971 A1* | 7/2003 | Liberman et al. ........... 29/419.1 |
| 2003/0212344 A1 | 11/2003 | Yuzhakov et al. |
| 2003/0217918 A1 | 11/2003 | Davies et al. |
| 2004/0002682 A1 | 1/2004 | Kovelman et al. |
| 2004/0039303 A1 | 2/2004 | Wurster et al. |
| 2004/0094432 A1 | 5/2004 | Neel et al. |
| 2004/0136866 A1 | 7/2004 | Pontis et al. |
| 2004/0146863 A1* | 7/2004 | Pisharody et al. ................. 435/6 |
| 2004/0200721 A1 | 10/2004 | Bhullar et al. |
| 2004/0254546 A1 | 12/2004 | Lefebvre |
| 2005/0183953 A1 | 8/2005 | Su et al. |
| 2005/0238537 A1* | 10/2005 | Say et al. ................... 422/82.02 |
| 2005/0261606 A1 | 11/2005 | Sohrab |
| 2005/0279647 A1 | 12/2005 | Beaty |
| 2005/0287065 A1 | 12/2005 | Suddarth et al. |
| 2006/0113187 A1 | 6/2006 | Deng et al. |
| 2006/0211933 A1 | 9/2006 | Zimmermann et al. |
| 2007/0027384 A1* | 2/2007 | Brister et al. ................. 600/365 |
| 2007/0087492 A1 | 4/2007 | Yamanaka |
| 2007/0096164 A1 | 5/2007 | Peters et al. |
| 2008/0027302 A1 | 1/2008 | Buse et al. |
| 2008/0167578 A1 | 7/2008 | Bryer et al. |
| 2008/0197024 A1 | 8/2008 | Simpson et al. |
| 2009/0018411 A1 | 1/2009 | Mace et al. |
| 2010/0270150 A1 | 10/2010 | Wang et al. |
| 2010/0274181 A1 | 10/2010 | Wang et al. |
| 2011/0180405 A1 | 7/2011 | Chinnayelka et al. |
| 2016/0029935 A1 | 2/2016 | Chinnayelka et al. |

FOREIGN PATENT DOCUMENTS

| | | |
|---|---|---|
| WO | WO 2010/033660 | 3/2010 |
| WO | WO 2010/033668 | 3/2010 |
| WO | WO 2010/033741 | 3/2010 |
| WO | WO 2010/033748 | 3/2010 |

OTHER PUBLICATIONS

Wang et al., Miniaturized Glucose Sensors Based on Electrochemical Codeposition of Rhodium and Glucose Oxidase onto Carbon-Fiber Electrodes, 1992, The American Chemical Society, vol. 64, pp. 456-459.*

International Search Report and Written Opinion of related International Application No. PCT/US2009/057253 mailed Nov. 2, 2009.

International Search Report and Written Opinion of related International Application No. PCT/US2009/057264 mailed Nov. 10, 2009.

International Preliminary Report on Patentability of related International Application No. PCT/US2009/057264 mailed Mar. 31, 2011.

International Search Report and Written Opinion of International Application No. PCT/US2009/057372 mailed Nov. 13, 2009.

International Preliminary Report on Patentability of related International Application No. PCT/US09/057382 mailed Mar. 31, 2011.

International Search Report and Written Opinion of International Application No. PCT/US09/057382 mailed Feb. 1, 2010.

International Preliminary Report on Patentability and Written Opinion of related International Application No. PCT/US2009/057372 mailed Mar. 31, 2011.

International Preliminary Report on Patentability Search Report and Written Opinion of related International Application No. PCT/US2009/057253 mailed Mar. 31, 2011.

Communication pursuant to Rules 161(2) and 162 EPC of related European Application No. 09815226.7 May 12, 2011.

Communication pursuant to Rules 161(2) and 162 EPC of related European Application No. 09815166.5 May 13, 2011.

Communication pursuant to Rules 161(2) and 162 EPC of related European Application No. 09815223.4 May 12, 2011.

Communication pursuant to Rules 161(2) and 162 EPC of related European Application No. 09815172.3 May 25, 2011.

Singh et al., "SiC-C Fiber Electrode for Biological Sensing", Feb. 22, 2007, Materials Science and Engineering C, Elsevier Science S.A., vol. 27, No. 3, pp. 551-557.

Isao Karube et al., "Integrated Microbiosensors for Medical Use", Dec. 1, 1989, Annals of New York Academy of Sciences, vol. 542, No. 9, pp. 470-479.

International Preliminary Report on Patentability and Written Opinion of International Application No. PCT/US2009/032991 mailed Aug. 19, 2010.

Extended Search Report of related European Application No. 09815223.4 dated Oct. 2, 2012.

Communication pursuant to Rules 70(2) and 70a(2) EPC of related European Application No. 09815223.4 dated Oct. 19, 2012.

Extended Search Report of related European Application No. 09815166.5 dated Oct. 22, 2012.

Extended Search Report of related European Application No. 09815226.7 May 9, 2014.

Sengupta, D.K., et al. "Laser Conversion of Electrical Properties for Silicon Carbide Device Applications", Jour. of Laser Applications, vol. 13, Jan. 1, 2011, pp. 26-31.

Office Action and Examination Search Report of related Canadian Application No. 2,735,666 Sep. 29, 2015.

Charlton et al., U.S. Appl. No. 15/071,188, titled: "Electrical Devices With Enhanced Electrochemical Activity and Manufacturing Methods Thereof," filed Mar. 15, 2016.

* cited by examiner

SEMICONDUCTOR BASED ANALYTE SENSORS AND METHODS

RELATED APPLICATIONS

The present application claims priority to U.S. Provisional Patent Application No. 61/026,081 filed Feb. 4, 2008, and entitled "SEMICONDUCTOR BASED ANALYTE SENSORS" which is hereby incorporated herein by reference in its entirety for all purposes.

FIELD OF THE INVENTION

The present invention relates to analyte detection, and more particularly to sensors for use in detecting analytes.

BACKGROUND OF THE INVENTION

The monitoring of analyte levels is an important part of numerous types of health diagnostics, such as diabetes care. Such monitoring typically involves using a sensor to detect a concentration level of an analyte in an in vitro or in vivo sample taken from a patient. Analyte sensors may function in various modes, including an amperometric mode, in which a current level that correlates to the analyte concentration in the sample is generated at a working electrode.

Analyte sensors may be employed discretely, for instance, by detecting the analyte concentration level in a single sample taken from the patient (e.g., by a pin-prick or needle), or continuously, by implanting the sensor in the patient for a duration of several days or more. Continuous monitoring offers the potential advantages of detecting certain health conditions that often go undetected by discrete monitoring, and the possibility of providing closed-loop control through immediate treatment of such conditions on an as needed basis. For example, if needed, insulin may be provided immediately to a diabetic patient continually monitored for hypoglycemia using an analyte sensor adapted to detect glucose levels.

Conventional analyte sensors used for continuous monitoring are typically formed from substrates (e.g., tantalum) that may have disadvantageous mechanical properties for manufacturing purposes or continuous monitoring applications. For example, tantalum substrates have low tensile strength, making it difficult to fabricate tantalum sensors with small dimensions (e.g., below a 350 micron diameter); thus, it may be difficult to fabricate sensors using conventional substrates at a size sufficiently small to avoid pain and/or discomfort during insertion and/or implantation.

Tantalum substrates are also susceptible to embrittlement if exposed to hydrogen. For example, when tantalum is used as a substrate material of an analyte sensor, care should be taken to completely coat the working electrode regions of the sensor with platinum or another anode material to avoid direct contact between the chemical reactants which produce current at the working electrode regions and the underlying tantalum substrate. As platinum and similar materials are expensive, these measures add considerably to the expense of conventional analyte sensors.

It would therefore be beneficial to provide an analyte sensor that has both robust mechanical properties and suitable electrical properties adapted for both in vivo and in vitro use.

SUMMARY OF THE INVENTION

In one aspect of the invention, an analyte sensor is provided that includes a substrate including semiconductor material that forms at least a portion of a conducting path for a working electrode of the analyte sensor.

In another aspect of the invention, an analyte sensor is provided that includes a substrate having a core composed of a conductive material, and a cladding composed of a semiconductor material that forms at least a portion of a conducting path for a working electrode of the analyte sensor.

In another aspect of the invention, an analyte sensor is provided that includes a substrate including a core comprised of conductive material; and a cladding comprised of semiconductor material, wherein the cladding forming at least a portion of a conducting path for a working electrode and the cladding has a tensile strength of at least 1,000 MPa.

In another aspect of the invention, an analyte sensor is provided that includes a substrate including semiconductor material; and an active region positioned on the substrate and adapted to be exposed to a fluid environment, the active region including an agent adapted to convert an analyte within the fluid environment into a product from which an electrical current may be generated.

In method aspect of the invention, a method of manufacturing an analyte sensor is provided. The method includes providing a substrate including semiconductor material; and applying an electrochemically-active layer on at least a portion of the substrate.

In another method aspect of the invention, a method of using an analyte sensor is provided. A method of using an analyte sensor includes providing an analyte sensor having a substrate including semiconductor material; and inserting at least a portion of the analyte sensor into a user's body.

Other features and aspects of the present invention will become more fully apparent from the following detailed description, the appended claims and the accompanying drawings.

DETAILED DESCRIPTION

According to the present invention, an analyte sensor is provided which has a substrate comprising semiconductor material. In some embodiments, the substrate may include a core including a conductive material, and a cladding including the semiconductor material. In some embodiments, the conductive material of the core may comprise carbon (e.g., graphite) and the semiconductor material may comprise silicon carbide. Other core and/or cladding materials may be used. The semiconductor material (e.g., cladding) may form a conductive path for one or more working electrodes of the analyte sensor. In some embodiments, the cladding may form at least a portion of a working electrode of the analyte sensor.

In one or more embodiments, the analyte sensor of the present invention may be adapted, by inclusion of suitable agent, such as a catalytic agent, to detect an analyte level (e.g., a glucose level), although it is intended that the analyte sensor may be used to detect other analytes (diagnostic or otherwise), such as, for example, glutamate and/or lactate or other analytes. The analyte sensor may be implanted in a patient for continuous analyte monitoring or alternatively may be employed discretely in either in vitro or in vivo tests. As described further below, the inventive analyte sensor employs a substrate that provides advantages in terms of size, flexibility, mechanical strength, reduced expense and/or electrochemical stability when compared to conventional analyte sensor substrates. In one or more embodiments, the analyte sensor of the present invention may be sufficiently small that it may be inserted into a patient without the use of a trocar. A trocar is a hollow cylinder with a sharply pointed end, often a three-sided point, used to introduce implements into blood vessels or body cavities.

Figure 1:
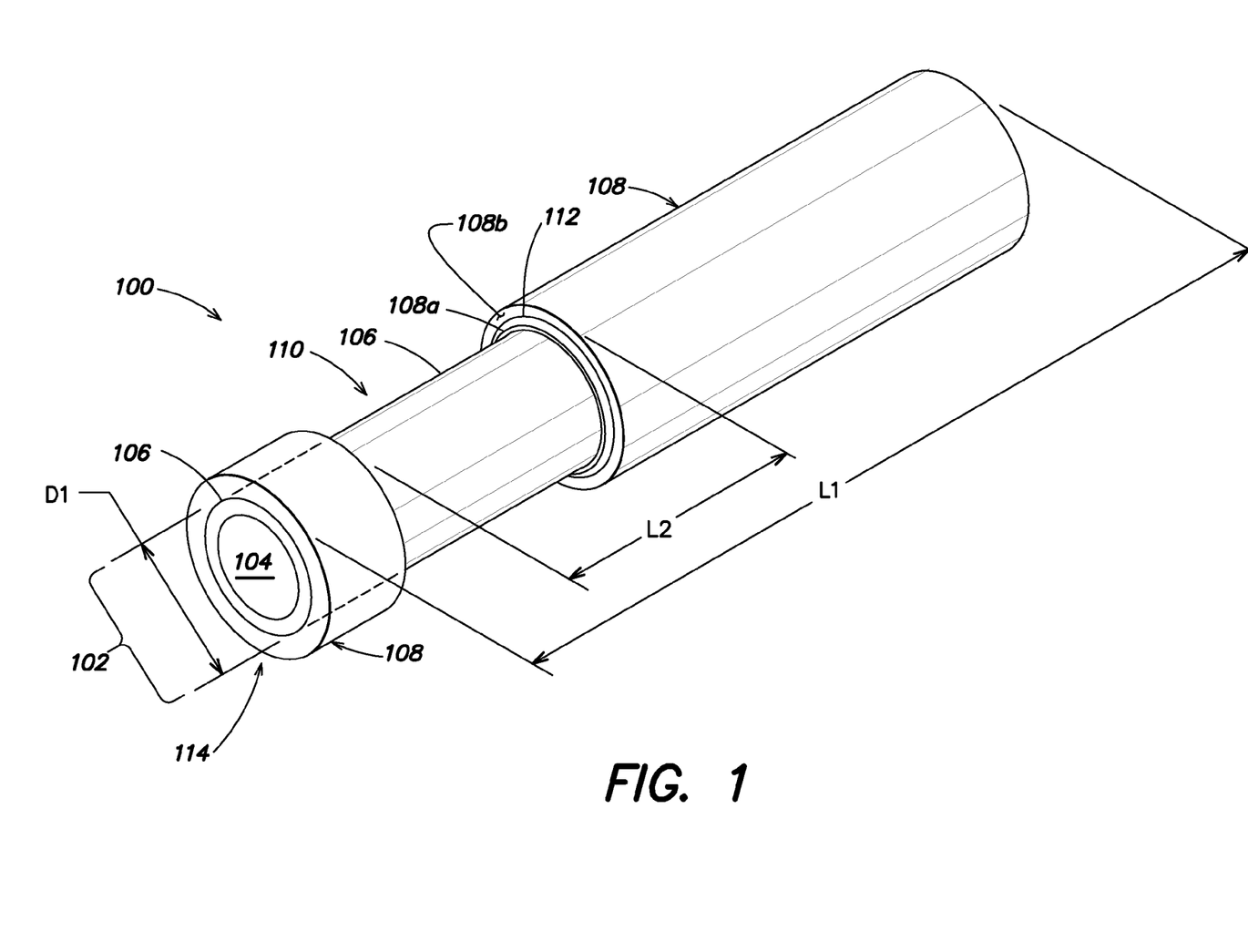
FIG. 1 is a perspective view of an exemplary analyte sensor according to an embodiment of the present invention.

FIG. 1 is a perspective view of an exemplary embodiment of an analyte sensor 100 provided according to the present invention. The sensor 100 includes a substrate 102 with a conductive core 104 surrounded by a cladding 106 comprising a semiconductor material. The sensor 100 of FIG. 1 is shown as being cylindrical. However, the analyte sensor 100 may be formed in other shapes, such as a planar strip having a central conductive core layer coated or otherwise surrounded by one or more semiconductor layers. Both the core 104 and the cladding 106 are able to convey electrical current.

In some embodiments, the substrate may take the form of a fiber. In some embodiments, the core 104 may comprise carbon (e.g., graphite), and the cladding 106 may comprise silicon carbide (SiC) in the form of a SiC fiber. The fiber may have a length longer than its width and both the core 104 and the cladding 106 may have a cylindrical shape, for example. Suitable SiC fibers are manufactured by Specialty Materials Inc. of Lowell, Mass., for example. However, the conductive material of the core 104 may also comprise other materials including metals such as copper or platinum, a conductive polymer, a polymer embedded with carbon nanotubes, or the like, and the cladding 106 may comprise other semiconductor materials including Group IV elements such as silicon and germanium, Group IV compounds such as silicon germanide (SiGe), and Group III-V compounds such as gallium arsenide (GaAs) and indium phosphide (InP), among others. In some embodiments, the substrate 102 may have a length (L1) of about 2.5 mm to 100 mm, about 5 mm to 100 mm, or even about 10 mm to 100 mm, and preferably about 50 mm. The substrate 102 may have a diameter (D1) of less than about 500 microns, less than about 250 microns, and in some embodiments, even less than about 150 microns. The diameter (D1) may range from about 50 microns to 500 microns, about 50 microns to 250 microns, about 50 microns to 150 microns, or even about 75 microns to 150 microns, although other dimensions may be used. In one or more embodiments, the core 104 and cladding 106 may be electrically insulated from one another by an intervening insulating layer (not shown). The materials for the core 104 and cladding 106 may be biocompatible.

The analyte sensor 100 may also include a protective layer 108 which largely covers the substrate 102, with one or more regions 110 along the substrate 102 being left uncovered. In some embodiments, the protective layer may add about 10 microns to 100 microns, or even about 20 microns to 100 microns, to the width of the analyte sensor 100, so that the total coated diameter of the sensor 100 may be less than about 250 microns, about 60 to 250 microns, about 85 to 250 microns, or even about 95 to 250 microns. At this diameter level, which is smaller than conventional needle gauges (sizes), the sensor 100 is minimally invasive and flexible, and thus causes little pain or discomfort when inserted or implanted. The relatively small diameter of the inventive analyte sensor 100 also allows implantation in areas of the body, including (but not limited to) the arm and thigh, which would not normally be considered as implantation sites for larger conventional devices. The protective layer 108 may comprise an insulator such as silicone rubber, polyimide, polytetrafluoroethylene (Teflon®), polyethylene, or any other suitable biocompatible dielectric. The protective layer 108 may be provided by dipping, spraying or other suitable application methods.

The region(s) not covered by the protective layer 108 (only one region being shown in FIG. 1) may form an active region 110 adapted to be exposed to a fluid environment indicative of an analyte level. To accomplish this end, the active region 110 may include an electrochemically active working electrode (not explicitly shown in FIG. 1) that is electrochemically sensitive to one or more chemical products derivable from the analyte present in an environment to which the analyte sensor 100 is exposed. The working electrode is adapted to generate an electrical signal corresponding to the analyte concentration level (as described further below). The active region 110 may be formed in a variety of shapes and sizes. In at least one embodiment (as shown), the active region forms an annular surface having a length (L2) of about 0.2 to 10 mm and which may extend entirely around the substrate 102. Other lengths may be used.

A reference electrode 112, which in one or more embodiments may also function as a counter electrode and may provide a return path for an electrical current, may be positioned on, or formed in, the protective layer 108. In the depicted embodiment, the protective layer 108 may include a base layer 108a functioning as an electrical insulating layer between the cladding 106 and the reference electrode 112, and one or more coatings or additional insulating layers 108b to cover the reference electrode 112. In some embodiments, the reference electrode 112 may comprise an Ag/AgCl coil, sheath, sputter coating and/or photolithography-defined coating, as is commonly used in the art. Other materials and configurations may be employed for the reference electrode 112.

The analyte sensor 100 may function as an amperometric sensor in which the reference electrode 112 provides a stable reference voltage and a current produced by an electrochemical reaction at the working electrode in the active region 110 is conveyed by the reference electrode 112 to a measurement device (not shown). The current may be used as an indicator of electrochemical activity at the working electrode. It is noted however, that the analyte sensor 100 of the present invention may also be used in other modes in which other parameters such as voltage, conductance, capacitance and/or impedance may be directly measured rather than (or in addition to) current.

As discussed further below, the active region 110 may include one or more agents, such as catalytic agents that promote conversion of the analyte into products that then undergo an electrochemical reaction or otherwise produce a current at the working electrode. One useful group of catalytic agents is the class of oxidase enzymes including, for example, glucose oxidase (which converts glucose), lactate oxidase (which converts lactate), and D-aspartate oxidase (which converts D-aspartate and D-glutamate). A more detailed list of oxidase enzymes which may be employed in the present invention is provided in U.S. Pat. No. 4,721,677, entitled "Implantable Gas-containing Biosensor and Method for Measuring and Analyte such as Glucose" to Clark Jr. which is hereby incorporated by reference herein in its entirety for all purposes. Agents and catalytic enzymes other than oxidase enzymes may also be used.

In embodiments in which glucose is the analyte of interest, glucose oxidase may be included in the active region 110. The reaction of this enzyme with glucose in the presence of oxygen produces hydrogen peroxide, which may react electrochemically at the working electrode in the active region 110 to yield an electrical current which may be conveyed through the cladding 106 and/or core 104. In cases where glucose dehydrogenase is used, electron transfer to the electrode is promoted. In this manner, the electrical activity at the working electrode in the active region 110 may provide an index of glucose concentration in the environment to which the analyte sensor 100 is exposed.

In some embodiments, the substrate 102 of the analyte sensor 100 has advantageous mechanical properties that allow the analyte sensor 100 to be fabricated with a small diameter (e.g., about 500 microns or less, about 250 microns or less, 150 microns or less, or even 100 microns or less). In embodiments in which a SiC cladding 106 is used, the substrate 102 may be fabricated and machined at such small diameters due to the high tensile strength of SiC being above 3,000 MPa, or even 3,200 MPa (e.g., about 3,450 MPa to 5,865 MPa). Other semiconductors having other tensile strengths (preferably above about 1,000 MPa, above about 2,000 MPa or even above about 3,000 MPa), or even tensile strength of at least 3200 MPa may be used. At this reduced diameter level, the substrate 102 may have a medium modulus sufficient to provide flexibility for bending or deformation, a high yield stress sufficient to enable recoil, and medium to high ultimate strength to prevent breakage due to bending or twisting both during insertion and during the period in which the analyte sensor 100 is worn by the patient for continuous monitoring purposes. Due to these properties, the inventive analyte sensor 100 may be implanted easily (without requiring a catheter or other implantation tool) and is flexible enough to move with and conform to the implanted tissue, thereby minimizing tissue damage.

To further facilitate implantation, in one or more embodiments, the front end 114 of the analyte sensor 100 may be cleaved at an angle or shaped into a sharp point to form a lancet, facilitating insertion and/or implantation of the analyte sensor 100 under the skin. In addition, in some embodiments, the semiconductor cladding 106 may be non-toxic, biocompatible (e.g., hemocompatible), and resistant to platelet adhesion, clotting and encapsulation. Due to these properties, the analyte sensor 100 provided by the present invention may be implantable for comparatively long time periods. For example, for anticipated short term use, the analyte sensor 100 may be implanted for about 3 to 7 days and for longer term use, the sensor 100 may be implanted for about a week or longer.

Figure 2:
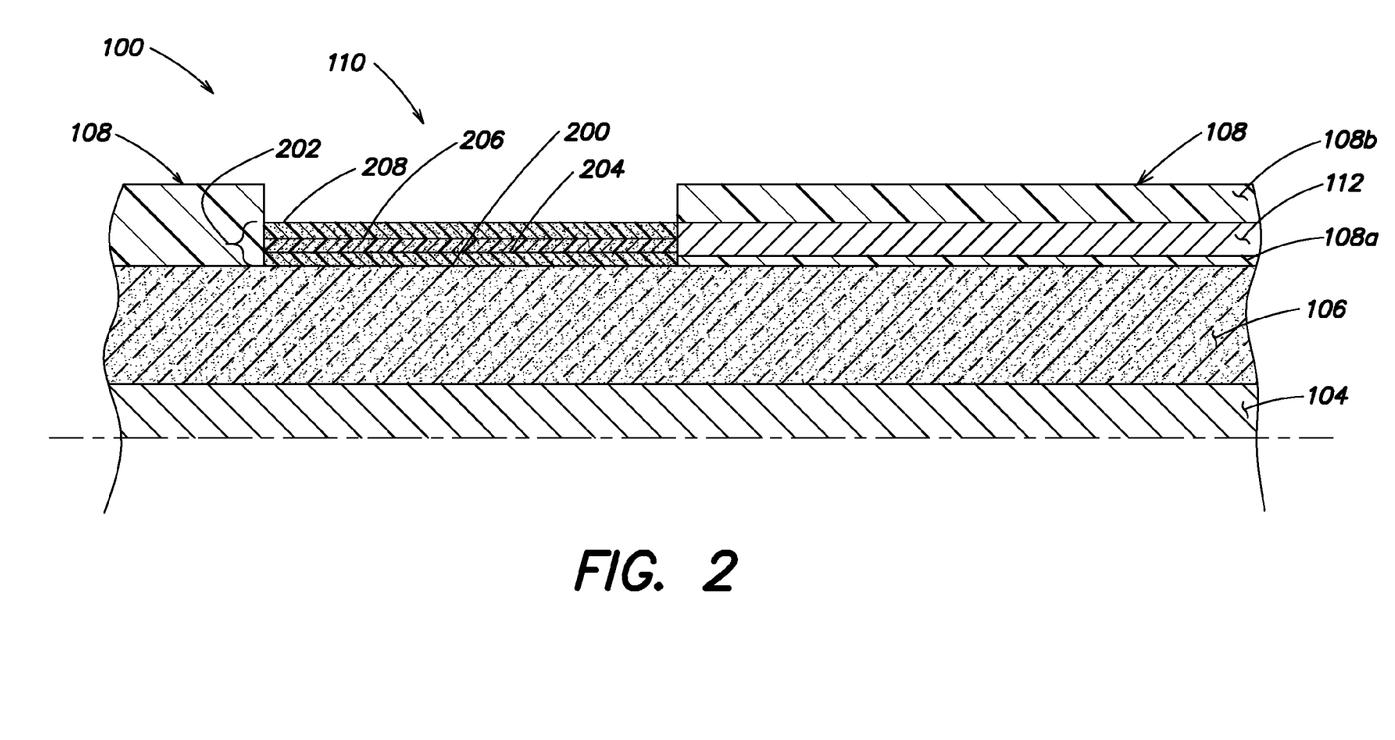
FIG. 2 is an enlarged partial cross-sectional view showing an active region of an exemplary analyte sensor according to an embodiment of the present invention.

FIG. 2 is an enlarged cross-sectional view of the active region 110 of an exemplary embodiment of the analyte sensor 100 according to the present invention. As shown, the active region 110 includes a longitudinal portion of the cladding 106, which in the depicted embodiment, forms the working electrode 200 of the sensor 100. One or more catalytic agents (described below) present in the active region 110 may promote conversion of an analyte into products that undergo an electrochemical reaction at the working electrode 200. The semiconductor material of the cladding 106 may be electrochemically active to some degree with respect to products of the catalytic reaction of the analyte. For example, at the active region 110, one or more catalytic agents (e.g., oxidases) may react with an analyte to produce hydrogen peroxide and one or more co-products. A measurable current may then be generated in the semiconductor material of the cladding 106 by the electrochemical reaction of the hydrogen peroxide. For example, in some embodiments, the inventors of the present invention have found that when SiC is employed as the cladding material, about 0.01 to 20 nanoamps (nA), or even 0.1 to 20 nanoamps (nA), of current may be generated by the reaction. Depending on the accuracy and precision of the measurement instrumentation employed, this current level may be sufficient in some applications to detect an analyte concentration level. However, care should be taken to ensure that the signal-to-noise ratio remains at an acceptable level as current may be generated at the cladding 106 by other reactions and events.

As noted above, one chemical (catalytic) reaction which allows glucose in particular to be detected is:

(1)

$$\text{analyte} + O_2 \xrightarrow{\text{oxidase enzyme}} H_2O_2 + \text{co-product}$$

where the catalytic agent (oxidase enzyme) facilitates the conversion of the analyte into a co-product (e.g., an acid) with hydrogen peroxide also produced as a detectable co-product of the reaction.

As can be discerned from formula (I), the reaction requires the presence of oxygen in order to yield detectable products. In some fluid environments in which the analyte sensor 100 is placed (e.g., interstitial fluid, plasma, etc.), the oxygen supply may be in deficit relative to the analyte. This deficit may limit the catalytic reaction from which detectable products are derived, and may result in inaccurate analyte concentration level determinations. Various techniques have been used to overcome this problem, some of which employ differentially or selectively permeable layers or membranes ('permselective layers') which are relatively more permeable to oxygen than to the analyte and thus serve to maintain the oxygen level in balance with the analyte concentration.

Referring again to FIG. 2, the active region 110 may include a stratified structure 202 having a plurality of layers 204, 206, 208 that, in combination, enable sufficient quantities of analyte, water and oxygen to react in the presence of one or more catalytic agents, such that a detectable product of the reaction (1) reaches the working electrode, enabling an accurate indication of the analyte concentration level to be measured. For example, the stratified structure 202 may comprise a plurality of polymeric layers that may be deposited by dip-coating, sputtering, spraying, electrochemical deposition, electrochemical polymerization, or other suitable methods. The layers 204, 206, 208 of the stratified structure 202 may be patterned in some embodiments (e.g., by laser ablation or photolithography) to limit these layers to the active region 110 and/or to create distinct structures within the layers 204, 206, 208.

In the depicted embodiment, a first permselective layer 204 may be applied and positioned directly over the cladding 106. The first permselective layer 204 may be made from one or more materials that are permeable with respect to oxygen and hydrogen peroxide but relatively impermeable with respect to larger molecules (e.g., urate, ascorbate, acetaminophen, etc.) which might interfere with detection. The first permselective layer 204 accordingly protects the cladding 106 from direct exposure to large molecules from the fluid environment and/or from the other layers 206, 208 of the structure 202. Suitable materials for the first permselective layer 204 may include one or more of cellulose acetate, nafion, polypyrrole, aniline, tyramine, o-aminopheono, o-phenylenediamine, or the like. This layer 204 may be applied by any suitable process to the cladding 106, such as by being deposited by dip-coating, sputtering, spraying, electrochemical deposition, or electrochemical polymerization.

A reactive layer 206, which may include one or more catalytic agents including, but not limited to, oxidase enzymes, is positioned above the first permselective layer 204. Other suitable agents such as catalytic agents or other biorecognition or bioactive agents may be used, depending on the detection application. For example, enzymes or detection chemistry for detecting analytes may be employed such as for testing of total cholesterol, uric acid, lipids, triglycerides, high density lipoprotein (HDL), low density lipoprotein (LDL), etc. The agents (e.g., catalytic agent(s)) may be immobilized within the reactive layer 206 using any of a variety of techniques in order to prevent diffusion of the catalytic agent(s) out of the reactive layer 206. Suitable techniques for applying and immobilizing the catalytic agent(s) in the reactive layer 206 may include, for example, coupling the catalytic agent(s) to the lattice of a polymer matrix such as a sol gel, cross-linking the agent(s) to a suitable matrix such as glutaraldehyde, and formation of an array between the catalytic agent(s) via covalent binding. In some embodiments, the reactive layer 206 may be formed from substantially the same polymeric material as the first permselective layer 204. However, in contrast to the first permselective layer 204, the analyte must be able to permeate the reactive layer 206 to some extent in order for a reaction between the analyte and catalytic agent to occur (such as reaction (1)). Accordingly, the reactive layer 206 may include one or more portions that are permeable to larger molecules. For example, U.S. Pat. No. 6,721,587, entitled "Membrane and Electrode Structure for Implantable Sensor" to Gough, hereby incorporated by reference herein in its entirety for all purposes, describes a technique in which discrete hydrophilic regions, permeable to large molecules and to oxygen, may be incorporated in an enzyme-containing layer. By controlling the number, size and shape of such hydrophilic regions, suitable permeability levels for the analyte in the reactive layer 206 may be achieved. In some embodiments, the reactive layer 206 may be formed using a layer-by-layer deposition technique, in which layers with different and/or alternating chemical properties such as charge, polarity, hydrophobicity, hydrophilicity, etc., are deposited over one another. The layers may form self-assembled monolayers and may include thiol linkages, for example. These layers may be formed by multiple means including: dip-coating, sputtering, spraying, electrochemical deposition, electrochemical polymerization and other suitable methods.

In some embodiments of the invention, mediators may be included in the active region 110 to promote the conversion of analyte to detectable products. Mediators comprise substances that act as intermediaries between the catalytic agent and the working electrode. For example, a mediator may promote electron transfer between the reaction center where the catalytic breakdown of the analyte takes place and the working electrode, and may thus enhance electrochemical activity at the electrode. Suitable mediators for mediating between enzymes (e.g., oxidase enzymes, dehydrogenase enzymes, fusion enzymes, etc.) and the working electrode may include one or more of the following: metal complexes including ferrocene and its derivatives, osmium complexes, quinines, phthalocyanines, organic dyes, as well as other substances. In one or more embodiments, the mediators may be incorporated in the first permselective layer 204 and/or the reactive layer 206. In an alternative embodiment, the mediators may be cross-linked along with catalytic agents directly to the working electrode, which in the depicted embodiment is the portion of the cladding 106 in the active region 110. In this alternative 'wired-electrode' embodiment, a distinct reactive layer may not be necessary as the catalytic agents are linked to the working electrode, and the permeability of the first permselective layer 204 may be adjusted to allow penetration of larger molecules to the vicinity of the working electrode.

Referring again to the embodiment of FIG. 2, the stratified structure 202 may also include a second permselective layer 208 applied to and positioned above the reactive layer 206. In some embodiments, the second permselective layer 208 may comprise silicone-based or organic polymers such as polyethylenes, polyurethanes, polypropylenes, polyterafluoroethylenes, block co-polymers, and the like which may have greater permeability with respect to smaller, non-polar molecules such as oxygen than with respect to larger, polar molecules such as various analytes including glucose, lactate and glutamate (among others). The second permselective layer 208 may optionally include one or more pores, perforations, channels or window regions in different areas (which may be patterned via laser ablation or photolithography, for example) so as to provide selective access for the analyte to permeate into the reactive layer 206 underneath. As the second permselective layer 208 may be exposed directly to the bodily environment in vivo, it is designed to be biocompatible. It is noted in this regard that even if there are defects in the second permselective layer 208 and/or in the stratified structure 202 as a whole such that the underlying semiconductor cladding 106 is exposed to the bodily or fluid environment, this is not a major concern in some embodiments, since many semiconductors including silicon, silicon carbide or the like are also biocompatible. In one or more embodiments, the second permselective layer 208 may be coated, at least partially, with polyethylene glycol to enhance biocompatibility as described in U.S. Pat. No. 6,934,572, entitled "Implantable Enzyme-based Monitoring System Having Improved Longevity Due to Improved Exterior Surfaces" to Schulman et al., which is hereby incorporated by reference herein in its entirety for all purposes. Other biocompatibility enhancement techniques may be used.

Figure 3:
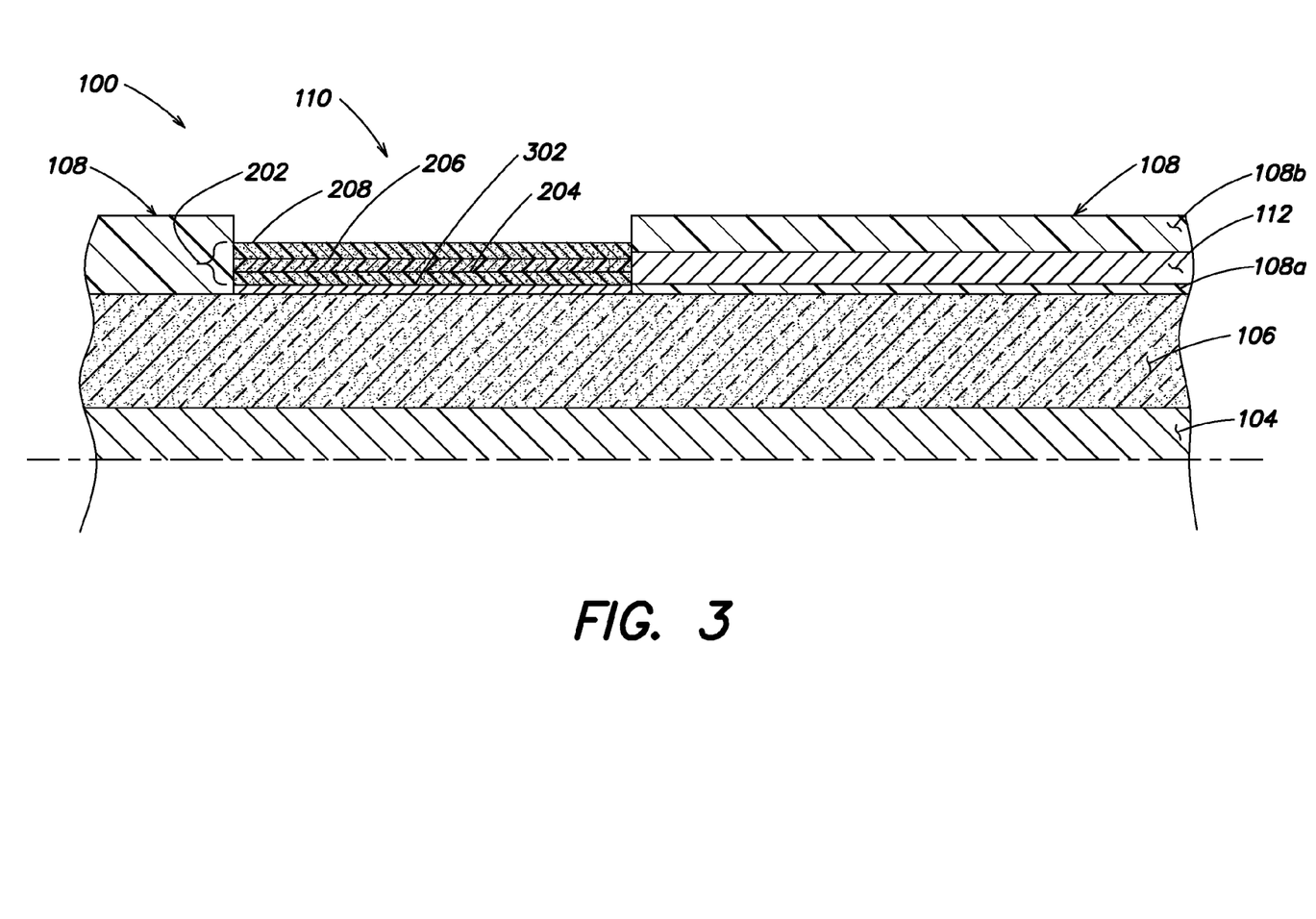
FIG. 3 is an enlarged partial cross-sectional view showing an active region of an exemplary analyte sensor according to another embodiment of the present invention.

FIG. 3 shows another exemplary embodiment of the analyte sensor 100 according to the present invention. The analyte sensor 100 of FIG. 3 includes an electrochemically-active layer 302 positioned directly over the cladding 106, and below the first permselective layer 204 to enhance electrochemical activity at the working electrode of the active region 110. In one or more embodiments, the electrochemically active layer 302 may react with (and generate current from) substantially all of the hydrogen peroxide or other detectable catalytic reaction by-product that reaches the layer 302 through the first permselective layer 204. In this case the electrochemically-active layer 302 may be considered to operate as the working electrode of the active region 110. In other embodiments, the electrochemically-active layer 302 may be considered to function in conjunction with the cladding 106 to generate and conduct electrical current, so that the working electrode may be considered to comprise a combination of the cladding 106 and the electrochemically active layer 302. According to one or more embodiments of the present invention, the electrochemical properties of the semiconductor material of the cladding 106 are such that interfering electrochemical reactions between the cladding 106 and the electrochemically active layer 302 do not occur. In this manner, background current and corrosive reactions are reduced or eliminated. This enables a stable signal to be generated at the working electrode having a high signal-to-noise ratio (e.g., about 2 or above).

According to some embodiments of the invention, the electrochemically-active layer 302 may comprise a noble metal such as platinum, gold, palladium and/or rhodium. Additionally or alternatively, the electrochemically-active layer 302 may comprise other substances known to enhance electrochemical activity and/or electron transfer, such as carbon nanotubes or conductive polymers. Platinum in particular has been found to be a useful material for forming an anode for detection of hydrogen peroxide. Conventional analyte sensors often employ platinum to form working electrodes. However, the substrates of conventional sensors, such as tantalum, may react strongly with detectable reaction products such as hydrogen peroxide (e.g., causing hydrogen embrittlement). Typically, a platinum layer of about 25 microns in thickness is deposited over active regions of conventional analyte sensors to ensure complete coverage without defects, adding considerably to the cost of the conventional sensors due to the expensiveness of platinum.

The analyte sensor 100 of the present invention dispenses with the need to provide such a large amount of platinum since the underlying substrate 102 does not suffer from the above mentioned drawbacks. The present inventors have determined that when a semiconductor cladding 106 is employed in a substrate 102, a substantially smaller amount of platinum may be used in comparison to conventional sensors, without sacrificing functionality. For example, in some embodiments, an electrically-active layer 302 may include only a sub-micron layer of platinum. In other embodiments, the electrochemically-active layer 302 may only partially cover the cladding 106 in the area of the active region 110. In some embodiments, when platinum is used as the electrochemically active material, the electrochemically-active layer 302 may cover between about 1% and 50%, and more preferably, between about 5% and 15% of the surface area of the active region 110. The amount of coverage may vary depending upon the electrochemical properties of the material used, with lower coverage more feasible for highly electrochemically active species. In some embodiments, a coverage level of between about 51% and 100% of the surface area of the active region 110 also may be used.

As discussed, due to the advantageous properties of the substrate 102 of the analyte sensor 100, a working electrode comprising an electrochemically-active layer 302 may contain considerably less material in comparison to conventional analyte sensors, and may only partially cover the underlying cladding 106. This allows rapid and relatively inexpensive techniques to be employed to apply and form the electrochemically-active layer 302, particularly since incomplete and/or non-uniform distribution of material in the layer 302 may be acceptable in many embodiments. Example techniques that may be employed include, but are not limited to, electroplating, sputtering, physical vapor deposition (PVD), chemical vapor deposition (CVD), and atomic layer deposition (ALD).

In addition, it is known that semiconductors can be doped to promote electrochemical activity. In one or more embodiments, a cladding 106 doped with an appropriate substance (e.g., boron) may be used in a substrate 102 of an analyte sensor 100. In some embodiments, a doped semiconductor cladding 106 may form one or more working electrodes on its own, or an electrochemically-active layer may be deposited over the doped cladding 106, as discussed above.

Figure 4:
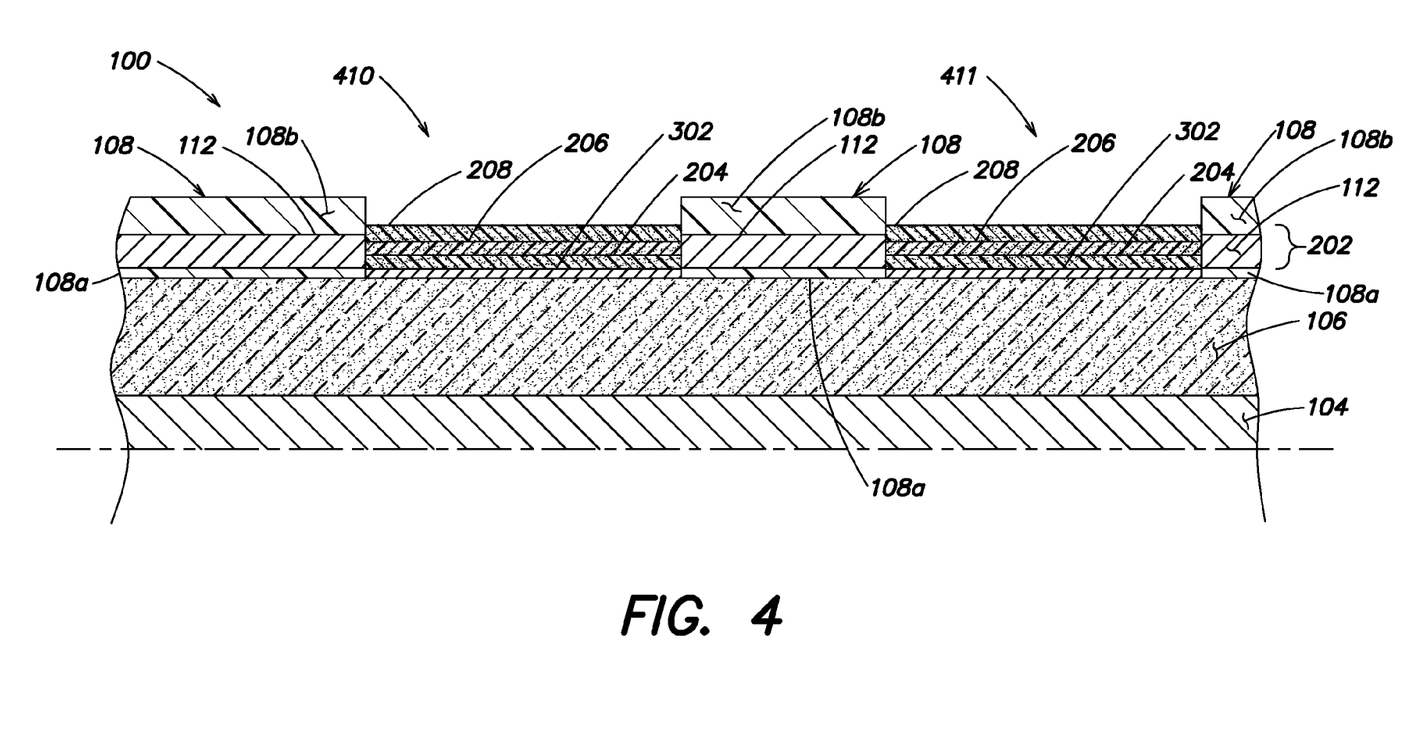
FIG. 4 is an enlarged partial cross-sectional view showing a plurality of active regions of an exemplary analyte sensor according to another embodiment of the present invention.

FIG. 4 shows another exemplary embodiment of the analyte sensor 100 according to the present invention which includes a plurality of active regions 410, 411. While two active regions 410, 411 are shown, the analyte sensor 100 of FIG. 4 may include more than two (e.g., three, four, etc.) active regions. Both active regions 410, 411 may be inserted in or implanted in a fluid environment indicative of an analyte concentration level simultaneously, and electrical signals may be generated in both regions 410, 411. Inclusion of a plurality of active regions 410, 411 may also provide redundancy so that the sensor 100 may still operate effectively if one or more of the active regions become defective due, for example, to loss of catalytic agents, electrode malfunction, etc. It is also noted that the active regions 410, 411 need not be identical to one another as shown. For example, one of the active regions may include an electrochemically-active layer 302 while the other may not, the active regions may be of different sizes, etc.

While the foregoing discussion has emphasized benefits of using analyte sensors according to the present invention for continuous analyte monitoring and implantation, it is to be appreciated that the inventive analyte sensors may be employed discretely as probes for in vitro tests. For example, the inventive analyte sensors may be dipped or otherwise placed in a fluid to test for the presence of hydrogen peroxide or other substances indicative of an analyte concentration level. Additionally, the inventive analyte sensors may be used in an array of biosensor probes.

In another method of using the analyte sensor, the analyte sensor having a substrate including semiconductor material may be provided, and at least a portion of the analyte sensor may be inserted into a user's body, such as into an arm, leg or other body part. In one method, the analyte sensor may be sufficiently small and robust so that the analyte sensor may be partially or fully inserted into the user's body without the use of a trocar. For example, the sensor may be inserted into a blood vessel.

The foregoing description discloses only exemplary embodiments of the invention. Modifications of the above disclosed apparatus and methods which fall within the scope of the invention will be readily apparent to those of ordinary skill in the art. For example, in some embodiments, the conductive core 104 of the substrate 102 may be eliminated, and the substrate 102 may include a hollow cladding region of semiconductor material or solid semiconductor material (e.g., the substrate 102 may be a hollow or solid cylinder of semiconductor material). Additionally, any known analyte detection chemistry may be used.

Accordingly, while the present invention has been disclosed in connection with exemplary embodiments thereof, it should be understood that other embodiments may fall within the scope of the invention, as defined by the following claims.

The invention claimed is:

1. An analyte sensor, comprising:
 a substrate including a core of conductive material and a cladding of a semiconductor material, wherein the cladding is disposed around the core,
 a protective layer disposed concentrically around, immediately adjacent, and in contact with the substrate, the protective layer including a base layer positioned between a reference electrode and the cladding, wherein an additional layer covers the reference electrode, and a working electrode formed from a portion of the cladding not covered by the protective layer, the working electrode being at least partially coated with an electrochemically-active layer formed from at least one of a noble metal, carbon nanotubes, and a conductive polymer, an active region positioned on the substrate and adapted to be exposed to a fluid environment, the active region including an agent on the electrochemically-active layer on the working electrode.

2. The analyte sensor of claim 1, wherein the cladding has a tensile strength of at least 1000 MPa.

3. The analyte sensor of claim 1, wherein the conductive material comprises carbon.

4. The analyte sensor of claim 1, wherein the substrate has a diameter of 150 microns or less.

5. The analyte sensor of claim 1, wherein the substrate has a diameter of about 75 to 150 microns.

6. The analyte sensor of claim 1, wherein the substrate has a length of about 2.5 mm to 100 mm.

7. The analyte sensor of claim 1, wherein the semiconductor material comprises silicon carbide.

8. The analyte sensor of claim 1, wherein the agent includes a catalyst agent, wherein the catalyst agent is adapted to convert an analyte within the fluid environment into a product from which an electrical current is generated at the working electrode.

9. The analyte sensor of claim 8, wherein the portion of the cladding forming the working electrode is 1% to 50% covered by the electrochemically-active layer.

10. The analyte sensor of claim 8, wherein the portion of the cladding forming the working electrode is 51% to 100% covered by the electrochemically-active layer which has a thickness of less than a micron.

11. The analyte sensor of claim 10, wherein the electrochemically-active layer includes at least one of platinum, gold, palladium, and rhodium.

12. The analyte sensor of claim 8, further comprising:

a mediator adapted to provide a transfer of electrons from the catalytic agent to produce an electrical current reading correlative with an analyte concentration level is derived.

13. The analyte sensor of claim 1, wherein the substrate is cylindrical.

14. The analyte sensor of claim 1, wherein the substrate is planar.

15. The analyte sensor of claim 1, wherein the substrate includes a point forming a lancet adapted to facilitate insertion.

* * * * *